United States Patent
Shim et al.

(10) Patent No.: US 9,746,408 B2
(45) Date of Patent: Aug. 29, 2017

(54) DUST SENSOR AND ELECTRONIC PRODUCT USING THE SAME

(71) Applicant: SAMSUNG DISPLAY CO., LTD., Yongin, Gyeonggi-Do (KR)

(72) Inventors: Hong Shik Shim, Seoul (KR); Jae Ik Lim, Hwaseong-si (KR); Jin Woo Choi, Seoul (KR)

(73) Assignee: Samsung Display Co., Ltd., Yongin, Gyeonggi-do (KR)

( * ) Notice: Subject to any disclaimer, the term of this patent is extended or adjusted under 35 U.S.C. 154(b) by 255 days.

(21) Appl. No.: 14/739,243

(22) Filed: Jun. 15, 2015

(65) Prior Publication Data
US 2016/0146715 A1 May 26, 2016

(30) Foreign Application Priority Data

Nov. 21, 2014 (KR) .......................... 10-2014-0163369

(51) Int. Cl.
*G01N 15/06* (2006.01)
*G06F 3/044* (2006.01)
*H04M 1/21* (2006.01)

(52) U.S. Cl.
CPC ............. *G01N 15/06* (2013.01); *G06F 3/044* (2013.01); *G01N 2015/0693* (2013.01); *H04M 1/21* (2013.01)

(58) Field of Classification Search
CPC G01N 15/06; G01N 2015/0693; G06F 3/044; H04M 1/21
See application file for complete search history.

(56) References Cited

U.S. PATENT DOCUMENTS

| | | | |
|---|---|---|---|
| 5,293,049 A | 3/1994 | Morey et al. | |
| 6,119,510 A * | 9/2000 | Carasso | G01N 15/0205 356/437 |
| 8,040,508 B2 * | 10/2011 | Holve | G01N 15/0205 356/336 |
| 2009/0229250 A1 * | 9/2009 | Yamakage | G01N 15/0205 60/276 |
| 2011/0058167 A1 * | 3/2011 | Knox | G01N 15/06 356/338 |
| 2011/0221889 A1 * | 9/2011 | Knox | G01N 21/53 348/135 |

FOREIGN PATENT DOCUMENTS

| | | |
|---|---|---|
| KR | 10-0351975 B1 | 8/2002 |
| KR | 10-2006-0043530 A | 5/2006 |
| KR | 10-1101988 B1 | 12/2011 |

* cited by examiner

*Primary Examiner* — Hezron E Williams
*Assistant Examiner* — David Z Huang
(74) *Attorney, Agent, or Firm* — Lee & Morse, P.C.

(57) ABSTRACT

A dust sensor includes a multi-wavelength light source, a receiver, and a controller. The light source emits light of different wavelengths. The receiver generates one or more acoustic wave measurement values based on acoustic waves irradiated from the light source to air particles. The controller controls at least one flickering cycle of the light source, determines the type particles based on the acoustic wave measurement values, and calculates the concentration of particles. The controller calculates the concentration of particles in proportion to an intensity of the acoustic wave measurement values, and determine the type of particles based on the acoustic wave measurement values. The acoustic waves are generated differently based on wavelengths of light emitted from the multi-wavelength light source.

23 Claims, 3 Drawing Sheets

DUST SENSOR AND ELECTRONIC PRODUCT USING THE SAME

CROSS-REFERENCE TO RELATED APPLICATION

Korean Patent Application No. 10-2014-0163369, filed on Nov. 21, 2014, and entitled: "Portable dust Senser and Cellular Phone Using The Same," is incorporated by reference herein in its entirety.

BACKGROUND

1. Field

One or more embodiments described herein relate to a portable dust sensor and a mobile phone including a portable dust sensor.

2. Description of the Related Art

Dust causes a variety of environmental, ecological, and health problems. This is especially true of the dust from explosions and accidents. Generally speaking, the finer the dust, the greater the harmful affect on the body. For example, dust and other forms of environmental contaminants (e.g., cadmium, lead, aluminum, copper, etc.) may mix with viruses and mold. Inhaling the dust may therefore cause various diseases, not the least of which include bronchitis, asthma, flu, laryngitis, rhinitis, and conjunctivitis.

SUMMARY

In accordance with one or more embodiments, a dust sensor includes a multi-wavelength light source to emit light of different wavelengths: a receiver to generate one or more acoustic wave measurement values based on acoustic waves irradiated from the multi-wavelength light source to air particles; and a controller to control at least one flickering cycle of the multi-wavelength light source, determine a type of one or more of the particles based on the one or more acoustic wave measurement values and calculate a concentration of the particles, wherein the controller is to calculate the concentration of particles in proportion to an intensity of the one or more acoustic wave measurement values and is to determine the type of the one or more of the particles based on the one or more acoustic wave measurement values, the acoustic waves to be generated differently based on the wavelengths of light emitted from the multi-wavelength light source.

The controller may control flickering cycles of the multi-wavelength light source to be different based on the wavelengths of light from the multi-wavelength light source, compare flickering cycles of the generated acoustic waves and the flickering cycles of the multi-wavelength light source, and determine the type of the one or more particles based on a flickering cycle distribution of the acoustic waves that depend on the flickering cycles of the multi-wavelength light source.

The multi-wavelength source may emit red, green, and blue light and infrared rays (IR), and the controller may determine the type of the one or more particles based on a first acoustic wave measurement value acquired by measuring a first acoustic wave generated according to a wavelength of the red light, a second acoustic wave measurement value acquired by measuring a second acoustic wave generated according to a wavelength of the green light, a third acoustic wave measurement acquired by measuring a third acoustic wave generated according to a wavelength of the blue light, and a fourth acoustic wave measurement acquired by measuring a fourth acoustic wave generated according to a wavelength of the IR.

The controller may control flickering cycles of the red, green, and blue light and the IR to be different from each other, measure a flickering cycle of the generated acoustic waves, and determine the type of the one or more particles according to a flickering cycle distribution of the acoustic waves respectively depending on the flickering cycles of the red, green, and blue light and the IR.

The controller may control the red light to be emitted with a first flickering cycle and is to determine the type of the one or more particles that are sensitive to the red light by measuring an acoustic wave generated with the first flickering cycle. The controller may control the green light to be emitted with a second flickering cycle and may determine the type of the one or more particles that are sensitive to the green light by measuring an acoustic wave generated with the second flickering cycle.

The controller may control the blue light to be emitted with a third flickering cycle and is to determine the type of the one or more particles that are sensitive to the blue light by measuring an acoustic wave generated with the third flickering cycle.

The controller may control the IR to be emitted with a fourth flickering cycle and is to determine the type of particles that are sensitive to the IR by measuring an acoustic wave generated with the fourth flickering cycle.

The controller may signal-divide one or more of the acoustic measurement values with a frequency domain, and calculate an entire concentration of the particles based on a signal convolution operation.

The multi-wavelength light source may include a first light source to emit red, green, and blue light and a second light source to emit infrared rays (IR). The particles may experience a volume change as the light of the multi-wavelength light source is absorbed and emitted to the particles, and the acoustic waves may be generated from a change in air density at a peripheral area of the particles according to the volume change.

The sensor may include a touch sensor to sense variation in touch capacitance caused by an approaching object, wherein the touch sensor may form static electricity by applying a voltage to a transparent electrode, the static electricity to form a cluster of particles.

In accordance with one or more other embodiments, a portable electronic device includes a display, comprising a receiver to generate acoustic wave measurement values by measuring acoustic waves generated from irradiation of light to air particles from a first light source; and a controller to control flickering cycles of the first light source, determine a type of one or more of the particles based on the acoustic wave measurement values, and calculate a concentration of the particles, wherein the controller is to calculate the concentration of particles in proportion to an intensity of the acoustic wave measurement values and is to determine the type of the one or more particles based on the acoustic wave measurement values measured, the acoustic waves to be generated differently according to wavelengths of the multi-wavelength light source.

The mobile phone may include a second light source to emit infrared rays (IR), wherein the multi-wavelength light source is to emit red, green, and blue light, and wherein the controller is to determine the type of the one or more particles based on a first acoustic wave measurement value acquired by measuring a first acoustic wave generated according to a wavelength of the red light, a second acoustic wave measurement value acquired by measuring a second acoustic wave generated according to a wavelength of the green light, a third acoustic wave measurement acquired by measuring a third acoustic wave generated according to a wavelength of the blue light, and a fourth acoustic wave measurement acquired by measuring a fourth acoustic wave generated according to a wavelength of IR.

The controller may control flickering cycles of the red, green, and blue light and the IR to be different from each other, measure flickering cycles of the generated acoustic waves, and determine the type of the one or more particles according to a flickering cycle distribution of acoustic waves that respectively depend on the flickering cycles of the red, green, and blue light and the IR.

The controller may control the red light to be emitted with a first flickering cycle and is to determine the type of the one or more particles that are sensitive to the red light by measuring an acoustic wave generated with the first flickering cycle.

The controller may control the green light to be emitted with a second flickering cycle and is to determine the type of particles that are sensitive to the green light by measuring an acoustic wave generated with the second flickering cycle.

The controller may control the blue light to be emitted with a third flickering cycle and is to determine the type of particles that are sensitive to the blue light by measuring an acoustic wave generated with the third flickering cycle. The controller may control the IR to be emitted with a fourth flickering cycle and is to determine the type of particles that are sensitive to the IR by measuring an acoustic wave generated with the fourth flickering cycle.

The controller may signal-divide the acoustic measurement value with a frequency domain, and calculate an entire concentration of the particles based on signal convolution operation. The particles may experience volume change as the light of the multi-wavelength light source is absorbed and emitted to the particles, and the acoustic wave may be generated from a change in air density at a peripheral area of the particles according to the volume change. The touch sensor may form static electricity by applying a voltage to a transparent electrode, the static electricity to form a cluster of particles. The electronic product may be a mobile phone.

BRIEF DESCRIPTION OF THE DRAWINGS

Features will become apparent to those of skill in the art by describing in detail exemplary embodiments with reference to the attached drawings in which.

DETAILED DESCRIPTION

Figure 1:
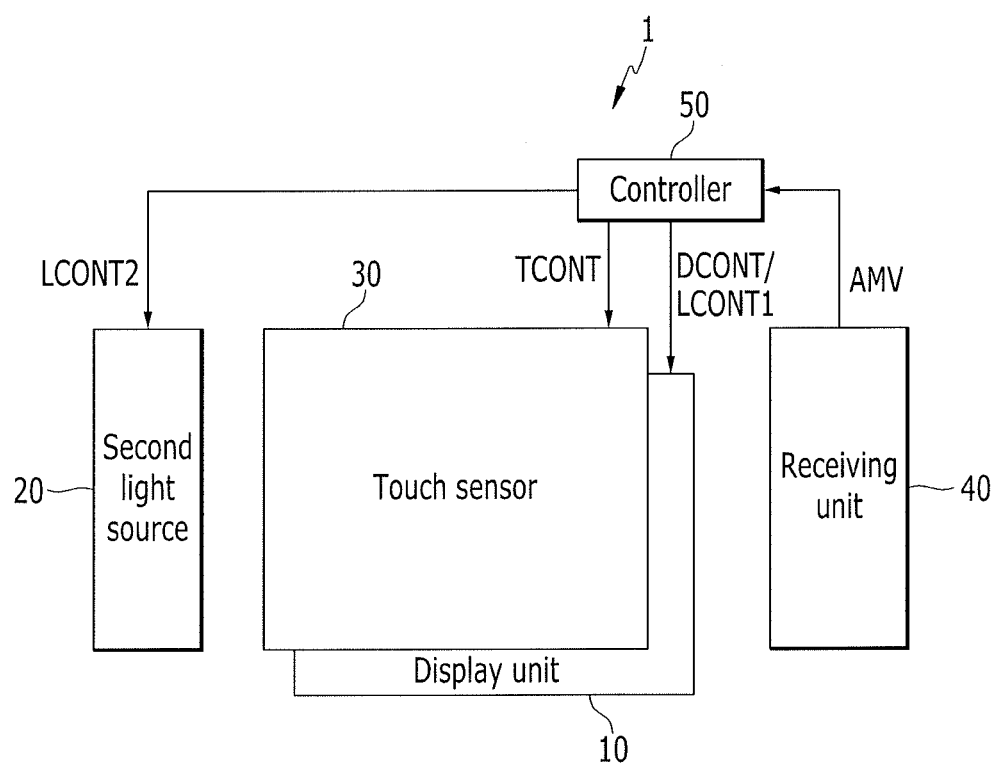
FIG. 1 illustrates an embodiment of a dust sensor.

Example embodiments are described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art. Like reference numerals refer to like elements throughout.

It is to be understood that when any component is referred to as being connected to or coupled to another component, it may be connected or coupled directly to the other component or may be connected or coupled to the other component with a further component intervening therebetween. On the other hand, it is to be understood that when one component is referred to as being connected or coupled directly to another component, it may be connected or coupled to the other component without a further component intervening therebetween.

Figure 3:
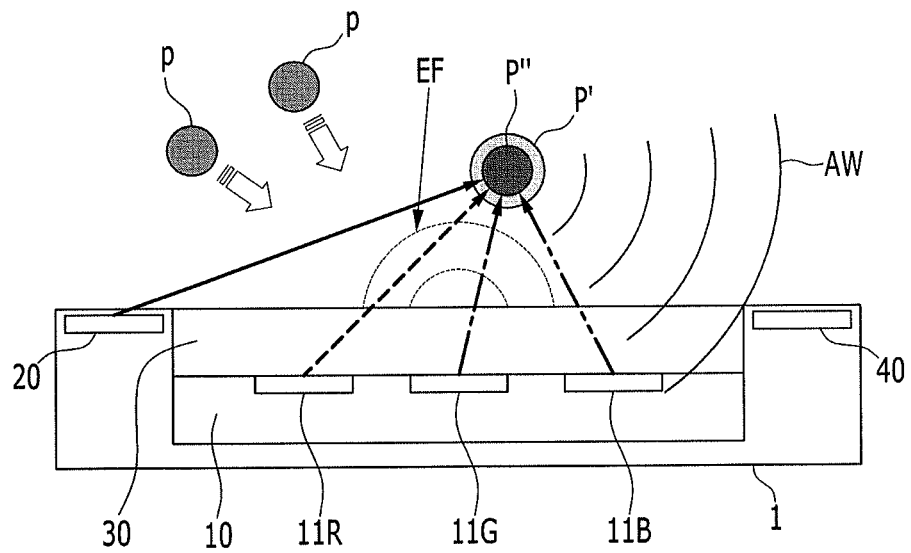
FIG. 3 illustrates an example of the operation of the dust sensor.

FIGS. 1 and 3 illustrate an embodiment of a dust sensor 1 included in an electronic product. The electronic device may be a mobile phone, a pad-type device, a tablet, notebook computer, media player or other type of portable device.

Referring to FIGS. 1 and 3, the dust sensor 1 includes a display unit 10, a second light source 20, a touch detector 30, a receiving unit 40, and a controller 50. The display unit 10 includes first light sources 11R, 11G, and 11B adjacent the touch detector 30. For example, the first light sources 11R, 11G, and 11B may be located under the touch detector 30. The display unit 10 outputs images corresponding to image data from an external source. The images are displayed, for example, based on a display control signal DCONT of the controller 50.

The display control signal DCONT may include a first light source control signal LCONT1. The first light sources 11R, 11G, and 11B include at least a red pixel 11R, a green pixel 11G, and a blue pixel 11B. According to the first light source control signal LCONT1, the red pixel 11R may emit light with a red wavelength of about 650 nm, the green pixel 11G may emit light with a green wavelength of about 550 nm, and the blue pixel 11B may emit light with a blue wavelength of about 450 nm. The first light sources 11R, 11G, and 11B may be self-emissive elements, e.g., organic light emitting diodes (OLEDs), light emitting diodes (LEDs), or laser diode (LDs).

The second light source 20 is outside the display unit 10 and includes an infrared ray (IR) LED. The second light source 20 may serve as an IR light source that emits IR according to a second light source control signal LCONT2. Thus, the first light sources 11R, 11G, and 11B and the second light source 20 may be used as multi-wavelength light sources.

Figure 2:
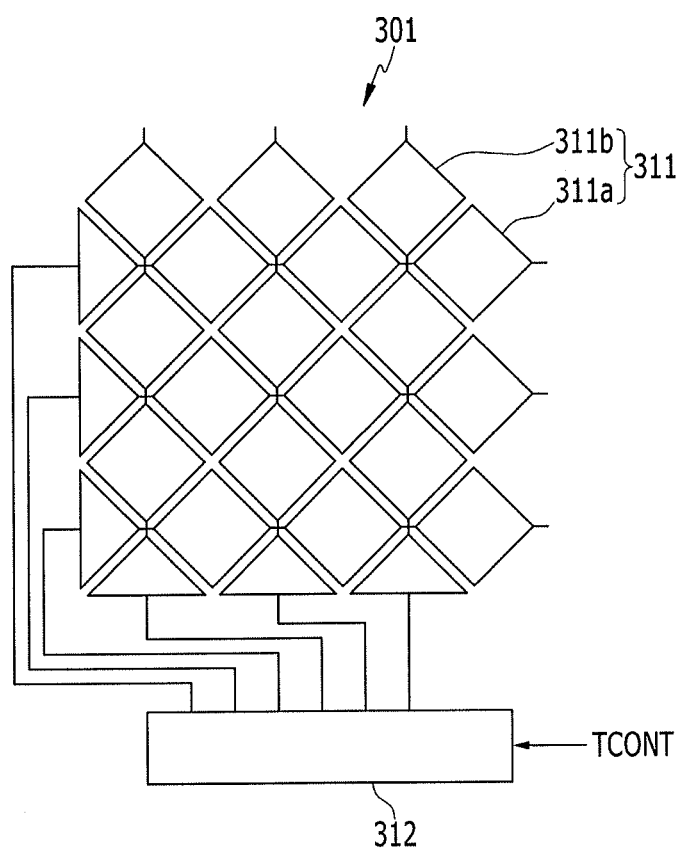
FIG. 2 illustrates an embodiment of a capacitive touch panel.

Referring to FIG. 2, the touch detector 30 includes a capacitive touch panel 301 which recognizes a touch location by detecting a change in touch capacitance produced by a touch input. The touch input may be, for example, a finger or stylus which nears or comes into contact with the upper surface of the display unit 10. The capacitive touch panel 301 forms a cluster of charged dust above the display unit 10 to improve sensitivity in measurement of particles P.

The capacitive touch panel 301 includes a transparent electrode 311 and a touch driver IC 312. The transparent electrode 311 includes a transparent metal such as indium tin oxide (ITO) or antimony tin oxide (ATO). The touch driver IC 312 recognizes a touch location. The transparent electrode 311 includes multiple types of electrodes, e.g., horizontal transparent electrodes 311a and vertical transparent electrodes 311b. The transparent electrode 311 has a predetermined shape, e.g., a rhombus shape.

The capacitive touch panel 301 recognizes a touch location by detecting the size of touch capacitance between the transparent electrode 311 and the finger or stylus. For example, the touch driver IC 312 applies a voltage between the horizontal transparent electrodes 311a and the vertical transparent electrodes 311b based on a touch control signal TCONT to form capacitance between the horizontal transparent electrode 311a and the vertical transparent electrode 311b. A touch location is then recognized by detecting a change in capacitance between a horizontal transparent electrode 311a and a vertical transparent electrode 311b that correspond to the touch location of the finger or stylus.

Referring to FIG. 3, the touch detector 30 forms an electrostatic field EF by applying a voltage to the transparent electrode 311 and forms a cluster of charged dust with particles P by the electric field EF. For example, when the touch driver IC 312 applies a potential (e.g., a positive potential, a second potential) that is different from a finger or stylus potential GND (e.g., a first potential) according to the touch control signal TCONT, the transparent electrode 311 has a potential that is different from the finger or stylus potential GND.

As a result, particles charged to the opposite potential (e.g., a negative potential, a third potential) of the potential of the transparent 311 move toward the touch panel 301 by electrostatic force to form a cluster of dust charged to the opposite potential of the transparent 311. Since the cluster of dust is formed above the display unit 10, sensitivity in measurement of particles P of the portable dust sensor may be improved.

The receiving unit 40 receives an acoustic wave (AW), generated from irradiation of light from the light sources 11R, 11G, 11B and 20 to the particle P, and generates an acoustic wave measurement value (AMV). For example, light irradiated to the particle P is absorbed by the particle P and then discharged as heat energy. When the light is absorbed to the particle P, the particle P expands (P'). The expanded particle P' contracts ((P")) as heat energy is discharged. The expansion and contraction of the particle P causes a change in concentration of air surrounding the particle P which corresponds to a change in volume of the particle P. When the irradiated light has periodicity, the air density changes with the same periodicity. The periodic change of air density is spread to the periphery of the particle P. If the periodicity corresponds to an acoustic area, such a spread forms an acoustic wave (WA).

The controller 50 generates a display control signal DCONT, a touch control signal TCONT, a first light source control signal LCONT1, and a second light source control signal LCONT2. The first light source control signal LCONT1 controls the wavelengths and flickering cycles of first light sources 11R, 11G, and 11B. The second light source control signal LCONT2 controls the wavelength and flickering cycle of the second light source 20. The controller 50 calculates the concentration of particles P and determines the type of particle P using the acoustic wave measurement value AMV).

The particle P generates an acoustic wave AW according to a wavelength that has a predetermined (e.g., relatively high or highest) sensitivity among wavelengths of light irradiated from the respective light sources. In addition, the particle P generates an acoustic wave AW with an intensity proportional to the concentration of particles P. The controller 50 calculates the concentration of particles P based on one or more characteristics of and the type of particles P.

For example, the controller 50 may calculate the concentration of particles P and determine the type of particles P using the acoustic wave measurement value (AMV) that is measured. This may be accomplished by controlling flickering cycles of the first light sources 11R, 11G, and 11B of red (R), green (G), and blue (B), and the IR light source 20 to be different from each other. For example, when the light source 11R irradiates red light to the particles P with a first flickering cycle (e.g., 1000 Hz), a particle P that is sensitive to a red wavelength generates an acoustic wave AW with the first flickering cycle. In this case, the intensity of the acoustic wave AW generated with the first flickering cycle is proportional to the concentration of particles P that are sensitive to the red wavelength.

When the light source G11 irradiates green light to the particles P with a second flickering cycle (e.g., 2000 Hz), a particle P that is sensitive to a green wavelength generates an acoustic wave AW with the second flickering cycle. In this case, the intensity of the acoustic wave AW generated with the second flickering cycle is proportional to a concentration of particles P that are sensitive to the green wavelength.

When the light source G11 irradiates blue light to the particles P with a third flickering cycle (e.g., 3000 Hz), a particle P that is sensitive to a blue wavelength generates an acoustic wave AW with the third flickering cycle. In this case, the intensity of the acoustic wave AW generated with the third flickering cycle is proportional to a concentration of particles P that are sensitive to the blue wavelength.

When the second light source 20 irradiates infrared ray (IR) with a fourth flickering cycle (e.g., 4000 Hz) to a particle, a particle that is sensitive to the IR generates an acoustic wave AW with the fourth flickering cycle. In this case, an intensity of the acoustic wave AW generated with the fourth flickering cycle is proportional to a concentration of particles P that are sensitive to the IR. The controller 50 signal-divides the acoustic wave measurement value (AMV) with a frequency domain, and performs a signal convolution operation to calculate the concentration of all the particles P and determines the type of particles.

In one embodiment, the controller 50 uses a characteristic that corresponds to black carbon, which is expected to be a main constituent of particles P. The characteristic of black carbon may be based on absorption, e.g., the characteristics of black carbon in absorbing a wavelength of a wide wavelength area from an ultraviolet (UV) ray wavelength to an IR wavelength (e.g., from UV to IR via a Vis wavelength area).

Different types of black carbons have different maximum absorption coefficients for each wavelength of irradiated light. In the portable dust sensor 1, multi-wavelength light emitted from the first light sources 11R, 11G, and 11B and the second light source 20 are irradiated to the particles P to determine the type of particle P that corresponds to a maximum wavelength absorbed in particle P.

The controller and other processing features of the embodiments disclosed herein may be implemented in logic which, for example, may include hardware, software, or both. When implemented at least partially in hardware, the controller and other processing features may be, for example, any one of a variety of integrated circuits including but not limited to an application-specific integrated circuit, a field-programmable gate array, a combination of logic gates, a system-on-chip, a microprocessor, or another type of processing or control circuit.

When implemented in at least partially in software, the controller and other processing features may include, for example, a memory or other storage device for storing code or instructions to be executed, for example, by a computer, processor, microprocessor, controller, or other signal processing device. The computer, processor, microprocessor, controller, or other signal processing device may be those described herein or one in addition to the elements described herein. Because the algorithms that form the basis of the methods (or operations of the computer, processor, microprocessor, controller, or other signal processing device) are described in detail, the code or instructions for implementing the operations of the method embodiments may transform the computer, processor, controller, or other signal processing device into a special-purpose processor for performing the methods described herein.

By way of summation and review, a microbubble may be used as a contrast agent for ultrasound imaging burst due to high intensity of ultrasound. Thus, the burst microbubble effectively acts as a contrast agent for photoacoustic imaging. However, this approach has proven to have drawbacks.

In accordance with one or more of the aforementioned embodiments, a portable dust sensor includes: a multi-wavelength light source emitting light of multi-wavelengths; a receiving unit generating an acoustic wave measurement value by measuring an acoustic wave generated from the multi-wavelength light irradiated to particles in the air; and a controller controlling a flickering cycle of the multi-wavelength light source, determining a type of the particle using the acoustic wave measurement value, and calculating concentration of the particles. The controller calculates the concentration of the particles in proportion to the intensity of the acoustic wave measurement value, and determines the type of particle based on an acoustic wave measurement value measured from an acoustic wave generated differently according to the wavelength of the multi-wavelength light source.

Example embodiments have been disclosed herein, and although specific terms are employed, they are used and are to be interpreted in a generic and descriptive sense only and not for purpose of limitation. In some instances, as would be apparent to one of skill in the art as of the filing of the present application, features, characteristics, and/or elements described in connection with a particular embodiment may be used singly or in combination with features, characteristics, and/or elements described in connection with other embodiments unless otherwise indicated. Accordingly, it will be understood by those of skill in the art that various changes in form and details may be made without departing from the spirit and scope of the present invention as set forth in the following claims.

What is claimed is:

1. A dust sensor, comprising:
a multi-wavelength light source to emit light of different wavelengths;
a receiver to generate one or more acoustic wave measurement values based on acoustic waves irradiated from the multi-wavelength light source to air particles; and
a controller to control at least one flickering cycle of the multi-wavelength light source, determine a type of one or more of the particles based on the one or more acoustic wave measurement values and calculate a concentration of the particles, wherein the controller is to calculate the concentration of particles in proportion to an intensity of the one or more acoustic wave measurement values and is to determine the type of the one or more of the particles based on the one or more acoustic wave measurement values, the acoustic waves to be generated differently based on the wavelengths of light emitted from the multi-wavelength light source.

2. The sensor as claimed in claim 1, wherein the controller is to:
control flickering cycles of the multi-wavelength light source to be different based on the wavelengths of light from the multi-wavelength light source,
compare flickering cycles of the generated acoustic waves and the flickering cycles of the multi-wavelength light source, and
determine the type of the one or more particles based on a flickering cycle distribution of the acoustic waves that depend on the flickering cycles of the multi-wavelength light source.

3. The sensor as claimed in claim 2, wherein:
the multi-wavelength source is to emit red, green, and blue light and infrared rays (IR), and
the controller is to determine the type of the one or more particles based on a first acoustic wave measurement value acquired by measuring a first acoustic wave generated according to a wavelength of the red light, a second acoustic wave measurement value acquired by measuring a second acoustic wave generated according to a wavelength of the green light, a third acoustic wave measurement acquired by measuring a third acoustic wave generated according to a wavelength of the blue light, and a fourth acoustic wave measurement acquired by measuring a fourth acoustic wave generated according to a wavelength of the IR.

4. The sensor as claimed in claim 3, wherein the controller is to control flickering cycles of the red, green, and blue light and the IR to be different from each other, measure a flickering cycle of the generated acoustic waves, and determine the type of the one or more particles according to a flickering cycle distribution of the acoustic waves respectively depending on the flickering cycles of the red, green, and blue light and the IR.

5. The sensor as claimed in claim 4, wherein the controller is to control the red light to be emitted with a first flickering cycle and is to determine the type of the one or more particles that are sensitive to the red light by measuring an acoustic wave generated with the first flickering cycle.

6. The sensor as claimed in claim 4, wherein the controller is to control the green light to be emitted with a second flickering cycle and is to determine the type of the one or more particles that are sensitive to the green light by measuring an acoustic wave generated with the second flickering cycle.

7. The sensor as claimed in claim 4, wherein the controller is to control the blue light to be emitted with a third flickering cycle and is to determine the type of the one or more particles that are sensitive to the blue light by measuring an acoustic wave generated with the third flickering cycle.

8. The sensor as claimed in claim 4, wherein the controller is to control the IR to be emitted with a fourth flickering cycle and is to determine the type of particles that are sensitive to the IR by measuring an acoustic wave generated with the fourth flickering cycle.

9. The sensor as claimed in claim 1, wherein the controller is to:
signal-divide one or more of the acoustic measurement values with a frequency domain, and
calculate an entire concentration of the particles based on a signal convolution operation.

10. The sensor as claimed in claim 1, wherein the multi-wavelength light source includes a first light source to emit red, green, and blue light and a second light source to emit infrared rays (IR).

11. The sensor as claimed in claim 1, wherein:
the particles are to experience a volume change as the light of the multi-wavelength light source is absorbed and emitted to the particles, and
the acoustic waves are generated from a change in air density at a peripheral area of the particles according to the volume change.

12. The sensor as claimed in claim 1, further comprising:
a touch sensor to sense variation in touch capacitance caused by an approaching object, wherein the touch sensor is to form static electricity by applying a voltage to a transparent electrode, the static electricity to form a cluster of particles.

13. An electronic product including a display, comprising:
a receiver to generate acoustic wave measurement values by measuring acoustic waves generated from irradiation of light to air particles from a first light source; and
a controller to control flickering cycles of the first light source, determine a type of one or more of the particles based on the acoustic wave measurement values, and calculate a concentration of the particles, wherein the controller is to calculate the concentration of particles in proportion to an intensity of the acoustic wave measurement values and is to determine the type of the one or more particles based on the acoustic wave measurement values measured, the acoustic waves to be generated differently according to wavelengths of the first light source.

14. The electronic product as claimed in claim 13, further comprising:
a second light source to emit infrared rays (IR),
wherein the first light source is to emit red, green, and blue light, and wherein the controller is to determine the type of the one or more particles based on a first acoustic wave measurement value acquired by measuring a first acoustic wave generated according to a wavelength of the red light, a second acoustic wave measurement value acquired by measuring a second acoustic wave generated according to a wavelength of the green light, a third acoustic wave measurement acquired by measuring a third acoustic wave generated according to a wavelength of the blue light, and a fourth acoustic wave measurement acquired by measuring a fourth acoustic wave generated according to a wavelength of the IR.

15. The electronic product as claimed in claim 14, wherein the controller is to control flickering cycles of the red, green, and blue light and the IR to be different from each other, measure flickering cycles of the generated acoustic waves, and determine the type of the one or more particles according to a flickering cycle distribution of acoustic waves that respectively depend on the flickering cycles of the red, green, and blue light and the IR.

16. The electronic product as claimed in claim 15, wherein the controller is to control the red light to be emitted with a first flickering cycle and is to determine the type of the one or more particles that are sensitive to the red light by measuring an acoustic wave generated with the first flickering cycle.

17. The electronic product as claimed in claim 15, wherein the controller is to control the green light to be emitted with a second flickering cycle and is to determine the type of particles that are sensitive to the green light by measuring an acoustic wave generated with the second flickering cycle.

18. The electronic product as claimed in claim 15, wherein the controller is to control the blue light to be emitted with a third flickering cycle and is to determine the type of particles that are sensitive to the blue light by measuring an acoustic wave generated with the third flickering cycle.

19. The electronic product as claimed in claim 15, wherein the controller is to control the IR to be emitted with a fourth flickering cycle and is to determine the type of particles that are sensitive to the IR by measuring an acoustic wave generated with the fourth flickering cycle.

20. The electronic product as claimed in claim 13, wherein the controller is to:
signal-divide the acoustic measurement value with a frequency domain, and
calculate an entire concentration of the particles based on signal convolution operation.

21. The electronic product as claimed in claim 13, wherein:
the particles are to experience volume change as the light of the first light source is absorbed and emitted to the particles, and
the acoustic wave is to be generated from a change in air density at a peripheral area of the particles according to the volume change.

22. The electronic product as claimed in claim 13, wherein the touch sensor is to form static electricity by applying a voltage to a transparent electrode, the static electricity to form a cluster of particles.

23. The electronic product as claimed in claim 13, wherein the electronic product is a mobile phone.

* * * * *